United States Patent [19]
Atkins et al.

[11] Patent Number: 6,124,506
[45] Date of Patent: Sep. 26, 2000

[54] SYNTHESIS OF GLYCOL ETHERS

[75] Inventors: Martin Philip Atkins, Ashford Middlesex, United Kingdom; Corinne Laurence Depege; Claude Rene Marcel Forano, both of Clermont-Ferrand, France

[73] Assignee: BP Chemicals Limited, London, United Kingdom

[21] Appl. No.: 08/999,550

[22] Filed: Dec. 18, 1997

Related U.S. Application Data

[63] Continuation of application No. PCT/GB96/01462, Jun. 17, 1996.

[30] Foreign Application Priority Data

Jun. 22, 1995 [GB] United Kingdom ............ 9512727

[51] Int. Cl.[7] .................................. C07C 43/10
[52] U.S. Cl. .................. 568/618; 568/613; 568/619; 502/62; 502/84
[58] Field of Search .................... 568/613, 617, 568/618, 619, 621, 622, 623, 624; 558/357; 585/440; 502/62, 80, 84

[56] References Cited

U.S. PATENT DOCUMENTS 4,774,212  9/1988  Drezdon .................... 502/62

FOREIGN PATENT DOCUMENTS 0 339 426 A2  4/1989  European Pat. Off. .
0 529 726 A1  8/1992  European Pat. Off. .
92/11224  7/1992  WIPO .

*Primary Examiner*—Sreeni Padmanabhan
*Attorney, Agent, or Firm*—Fay, Sharpe, Fagan, Minnich & McKee, LLP

[57] ABSTRACT

This invention relates to a process for making glycol ethers by reacting an olefin oxide with an alcohol over a catalyst comprising a layered double hydroxide (LDH) clay with its layered structure intact and having interlamellar anions at least some of which are metal anions or (poly)oxometallate anions. In the LDH clays, the interlamellar anions present are inorganic metal anions, oxometallate or polyoxometallate anions and include inter alia one or more of the following anions: chromium, vanadium, molybdenum and phosphorus, and (poly)oxoanions thereof. A copper-chromium hydrotalcite anionic clay or a magnesium-aluminium hydrotalcite anionic clay exchanged with (poly)oxometallate anions are preferred.

16 Claims, No Drawings

SYNTHESIS OF GLYCOL ETHERS

This application is a continuation of co-pending International Application No. PCT/GB96/01462 filed on Jun. 17, 1996.

This invention relates to a process for the synthesis of glycol ethers over intercalated metal oxides or hydroxides.

Glycol ethers are versatile molecules which combine the best solvency features of alcohols and ethers. Glycol ethers have miscibility and solvency for a wide range of organic chemicals as well as water. For these reasons, glycol ethers figure prominently in the (i) surface coating industry as active solvents for resins, (ii) brake fluid industry as solvents, (iii) petroleum industry as anti-icers in various petroleum based fuels, (iv) automotive industry as anti-freezes and (v) speciality products for use in households. It is well known that such glycol ethers can be produced by the reaction of an alcohol with an olefin oxide in the presence of an acidic or basic catalyst.

One of the most widely studied inorganic materials for their catalytic activity is the cationic clays. These clays comprise negatively charged metal silicate sheets intercalated with hydrated cations, eg the smectite clays.

A further class of well known clays are the anionic clays which are the intercalated metal oxides or hydroxides, especially layered double hydroxides (hereafter "LDHs"). These anionic clays are different from the conventional cationic clays in that these comprise positively charged double hydroxide sheets intercalated with anions and, as such, form a complementary class of materials to conventional cationic clays. Such compounds are described in eg "Anionic Clay Minerals", by Reichle, W T, "Chemtec", January 1986 and have the empirical formula:

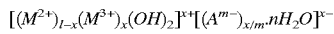
$$[(M^{2+})_{1-x}(M^{3+})_x(OH)_2]^{x+}[(A^{m-})_{x/m} \cdot nH_2O]^{x-}$$

Such compounds consist of positively charged metal oxide or hydroxide sheets with intercalated anions and water molecules. The positively charged layers are brucite-like [Mg(OH)$_2$] with trivalent cations substituting for divalent cations in octahedral sites of the hydroxide sheet. Sorption of hydrated anions renders the structure electrically neutral.

A wide range of such LDHs containing various combinations of the divalent cations $M^{2+}$ (eg $Mg^{2+}$, $Zn^{2+}$, $Cu^{2+}$, $Ni^{2+}$, $Fe^{2+}$, $Co^{2+}$ etc) and trivalent cations $M^{3+}$ (eg $Al^{3+}$, $Cr^{3+}$, $Fe^{3+}$ etc) and anions $A^{m-}$ (eg halogens, oxoanions, organic anions etc) can be synthesised either by direct crystallization from aqueous solutions thereof or by anion-exchange of a pre-crystallized LDH Clay (cf. K J Martin and T J Pinnavaia "J Am Chem Soc", 108, p. 541 (1986)).

The natural minerals of this type containing $Mg^{2+}$, $Al^{3+}$ or $CO_3^{2-}$ ions are called hydrotalcite [Mg$_6$Al$_2$(OH)$_{16}$] CO$_3$.4H$_2$O, and account for the predominate nomenclature in the literature of "hydrotalcite-like" compounds with a similar structure.

A large number of publications disclose that calcined LDHs have catalytic activity. For instance, U.S. Pat. No. 4,458,026 discloses that catalysts prepared by calcination of hydrotalcite-like compounds may be used to perform aldol condensations. JP-A-54111047 describes the preparation of alkylene glycol ether acetates using calcined LDHs. Similarly, EP-A-339426 discloses the use of calcined hydrotalcite for the ethoxylation and/or propoxylation of compounds containing active hydrogen atoms. Naturally-occurring LDH clays contain mainly carbonate anions in their interlamellar domain. Such materials normally have low activity as catalysts for the preparation of glycol ethers; it was believed that calcination enhances their activity.

Calcination of LDHs can be carried out over a wide range of temperatures, eg from 200–600° C., depending upon their structure and composition, and usually leads to the reversible collapse of their layered structure (Sato et al, Reactivity of Solids, 2, pp 253–260 (1986) and Sato et al, Ind. Eng. Chem., Prod. Res. Dev., 25, pp89–92 (1986)) and results in the formation of a spinel $M^{2+}M_2^{3+}O_4$, together with free $M^{2+}O$. All the above documents require that the LDHs be used as a catalyst in the calcined form, ie in a form having a collapsed layered structure.

Our prior published EP-A-0515636 describes the use of such double hydroxide clays comprising magnesium and aluminium in their framework structure in their uncalcined form for producing glycol ethers by reacting an alcohol with an olefin oxide when such clays have an anion of the reactant alcohol incorporated in their interlamellar space. Such clays as synthesised normally have carbonate anions in the interlamellar space but this is exchanged with the anions of the reactant alcohol by conventional ion-exchange techniques.

JP-A-H1-304043 discloses that hydrotalcite-like compounds carrying copper ions and in which hydroxyl ions are present at anion exchange sites catalyse the vapour-phase hydrolysis of aromatic halides.

A further set of such compounds in which the LDH clays have magnesium and aluminium atoms in their framework and which have anions of chloride, sulphate, nitrate, carbonate, terephthalate, and oxides of vanadium and/or molybdenum (the so-called "pillars") incorporated in their interlamellar space and are described in U.S. Pat. No. 4,774,212 and U.S. Pat. No. 4,843,168. The compounds described in these documents are different from those in EP-A-0515636 because these relate to pillared clays as against EP-A-0515636 which make no reference to pillared clays. These US patents describe the synthesis of these pillared clays and the use thereof as catalysts in some organic reactions such as eg dehydrogenation or ammoxidation of hydrocarbons, in particular aromatic hydrocarbons.

It has now been found that hydrotalcite anionic clays having hydroxides of copper and chromium in their framework structure can be produced, which clays for the purposes of the present invention can also be termed as LDH clays, and can also be converted into pillared clays by incorporation in their interlamellar space of large anions, especially metal anions and (poly)oxometallate anions. Furthermore, it has been found that such hydrotalcite clays which have hydroxides of magnesium, aluminium, copper and/or chromium in their framework and which have metal anions or (poly)oxometallate anions in the interlamellar space thereof, especially in their uncalcined form, are useful catalysts for producing glycol ethers.

Accordingly, the present invention is a process for making glycol ethers said process comprising reacting an olefin oxide with an alcohol over a catalyst comprising an LDH with its layered structure intact and having interlamellar anions at least some of which are metal anions or (poly)oxometallate anions.

The olefin oxide used as reactant is suitably ethylene, propylene and/or a butylene oxide.

The alcohol used for the reaction is suitably an aliphatic, cycloaliphatic or an aromatic alcohol and may be a mono-di- or poly-hydric alcohol. Monohydric alcohols are preferred. Specific examples of alcohols include the C1–C6 alcohols, especially, methanol, ethanol, the isomeric propanols and the isomeric butanols. The alcohol is suitably used in a molar excess if the desired end product is a monoglycol ether. In general, the molar ratio of alcohol to the olefin oxide is suitably at least 2:1 and is preferably in the range from 4:1 to 15:1, most preferably in the range from 5:1 to 12:1.

The surprising feature of this invention is the effectiveness of the uncalcined LDHs as catalysts for this reaction which is contrary to the earlier teachings noted above. Thus in the LDHs, the interlamellar anions present are inorganic metal anions, oxometallate or polyoxometallate anions and suitably include inter alia one or more of the following anions: chromium, vanadium, molybdenum and phosphorus, and (poly)oxoanions thereof The terms (poly) oxoanions and (poly)oxometallate anions are meant to include both oxoanions and oxometallate anions and the polyoxo derivatives thereof. For instance, a copper-chromium hydrotalcite anionic clay when exchanged with (poly)oxometallate anions, results in materials which have considerably improved selectivity as catalysts for the reaction of alcohol with olefin oxides. Such an ion-exchange can be carried out by conventional techniques on a precursor such as, eg by starting with a chloride precursor (which is readily synthesised by co-precipitation), a terephthalate precursor or a dodecylsulphate precursor.

Methods of preparing hydrotalcite anionic clays are well known in the art. One such method is described in U.S. Pat. No. 4,458,026. In general, solutions of soluble salts of divalent and trivalent metals are mixed together with a solution of a base such as eg sodium hydroxide and/or sodium carbonate at a controlled pH value or range. The resulting mixture is vigorously stirred at room temperature until a slurry is formed which is then optionally heated, suitably between 50° C. and 200° C. for several, until sufficient crystallisation occurs to form an LDH. The resulting LDH is then filtered, washed and dried and generally has a chloride or a carbonate as the interlamellar anion. Materials containing other ions may be prepared either by ion-exchange or by adapting the synthesis method so that the desired ions are incorporated in the interlamellar domain.

Other methods of synthesis of such LDHs in which double hydroxides of magnesium and aluminium are present in the framework are described in U.S. Pat. No. 4,774,212 and U.S. Pat. No. 4,843,168 and in which metal anions or (poly)oxometallate anions may be incorporated as pillars in the interlamellar space are referred to above.

The process of the present invention is suitably carried out in the liquid phase. The optimum reaction temperature will depend upon the reactants used but will generally be in the range from ambient to about 250° C. suitably from 50° C. to 150° C. The reaction can be carried out at a pressure in the range from atmospheric to about 50 bar (5000 KPa).

The process of the present invention can be used for instance for the reaction of butan-1-ol with one or more units of ethylene oxide to make butyl-monoglycol ether (BMGE), di-glycol ether(BDGE), tri-glycol ether etc. The reaction proceeds particularly smoothly with very high selectivity when making the monoglycol ether.

The present invention is further illustrated with reference to the following

EXAMPLES

Example 1 a. Preparation of the chloride precursor 40 ml of a mixture of 1 M $Cu(NO_3)_2.3H_2O$ and 1 M $CrCl_3.6H_2O$ solutions in a mole ratio of 2:1 respectively were added at a constant flow (4 ml/hr) in a beaker containing 100 ml of a 2 M KCl aqueous solution. At a fixed pH of 5.5, the copper-chromium chloride LDH was precipitated by adding 40 ml of a 2 M NaOH aqueous solution to the KCl solution using an automated titrator at room temperature under vigorous stirring. The addition was completed in 10 hours and the mother liquor was aged under the same conditions for 14 hours. Three successive washings using 250 ml of fresh distilled and decarbonated water were performed through centrifugation at 4000 rpm during 1 hour. The recovered gel was slowly dried in a fan oven at 60° C. The oven dried material was then broken down and sieved to collect particles of the size within the 0.5–1.0 mm range. The X-ray diffraction pattern (XRD) of this material showed it to be hydrotalcite with a $\delta(003)$ spacing of 7.70 Å.

b. Preparation of the chromate phase

The material prepared in 1(a) above (1g) was suspended in an aqueous solution (0.1 M, 100 ml) of $(CrO_4)^{2-}$ anion. The pH of this solution was maintained at a value of 8.5 during 3 hours using a 1 M NaOH aqueous solution at room temperature. The resulting product was then washed and dried at 60° C. as previously described in 1(a) above in order to obtain pellets which had a particle size between about 0.5 and 1.0 mm. The XRD pattern was typical of a hydrotalcite anionic clay with a $\delta(003)$ spacing of 8.42 Å.

c. Preparation of the dichromate phase

The procedure described in 1(b) above was repeated with a solution (0.1 M, 100 ml) of a dichromate anion maintained at a pH value of 4.5 by the addition of 1 M nitric acid. The XRD pattern was very similar to that of the chromate phase in 1(b) above with a $\delta(003)$ spacing of 8.95 Å.

d. Preparation of the pyrovanadate phase

The material prepared in 1(a) above (1 g) was suspended in an aqueous solution (0.1 M, 100 ml) of sodium vanadate. The pH of the solution was maintained by the addition of 1 M sodium hydroxide solution at a value of 10 over 3 hours at room temperature with vigorous stirring in order to intercalate the pyrovanadate anionic species, $(V_2O_7)^{4-}$. The washing and the pelleting procedure used was the same as described previously. The XRD pattern of this product showed a $\delta(003)$ spacing of 7.62 Å.

e. Preparation of the decavanadate phase

The material prepared in 1(a) (1 g) was suspended in an aqueous solution of 0.1 M terephthalic acid (100 ml). The pH was maintained at a value of 7.5 using 2 M NaOH solution during 5 hours at room temperature with vigorous stirring. The XRD pattern of the terephthalate phase thus obtained showed $\delta(003)$ spacing of 13.95 Å which facilitated the insertion of a voluminous decavanadate anion.

In order to obtain the decavanadate phase, the terephthalate phase (1 g) was suspended in an aqueous solution of 0.1 M sodium metavanadate (100 ml) maintained by the addition of dilute nitric acid at a pH value of 4.5 during 3 hours at room temperature. The subsequent treatments of washing and drying were carried out in a manner identical to those described in 1(d) above. The XRD pattern of the resulting product, which was not well crystallised, showed a $\delta(003)$ spacing of 11.61 Å.

f. Preparation of the heptamolybdate phase

The terephthalate phase prepared in 1(e) above (1 g) was suspended in an aqueous solution (0.1 M, 100 ml) of $Na_2MoO_4.2H_2O$. The pH of the solution was maintained at 4.5 by addition of dilute nitric acid over 3 hours at room temperature in order to keep the heptamolybdate anion, $[Mo_7O_{24}]^{6-}$, so formed in solution. The subsequent washing and drying treatments were carried out in a manner identical to those described in 1(d) above. The XRD pattern of the resulting product showed a $\delta(003)$ spacing of 12.77 Å.

g. Production of Glycol Ethers using the Catalysts 1(a)–(f) above

The above catalysts were tested for their ability to promote the epoxidation of alcohols in a stainless steel reactor (0.9 cm internal diameter) fitted with a thermowell. The catalyst bed volume used was 5 cm$^3$ in each case. The reaction was carried out using a mixed liquid feed prepared under pressure consisting of butan-1-ol (6 moles) and ethylene oxide (1 mole). The ethylene oxide co-feed was maintained in the liquid phase in the feed pot by having a 10 barg (1000 KPa) nitrogen head pressure. The reactor was initially pressurised to 3000 KPa (30 barg) at room temperature using the mixed feed. When this reactor pressure had been attained and stabilized, the liquid feed was pumped into the reactor at the rate of 10 cm$^3$/hour (LHSV=2). The reactor temperature was then slowly (at about 1° C. per minute) increased to 120° C. over a period of about 2 hours. When steady state was reached at this temperature and pressure (which corresponded to 0 hours on-stream), aliquots of the reaction mixture were sampled and analysed at regular intervals. The samples were analysed using a Pye-Unicam 4500 gas chromatograph fitted with a WCOT fused silica capillary column (50 m, 0.25 mm internal diameter, CP-Sil-5) operating with a temperature programme (80° C. for 10 minutes, ramping at the rate of 6° C./minute to 250° C.) to determine the relative amounts of mono-glycol ether, higher-glycol ethers and by-products formed. Mass balances were typically 98% or higher for any test period. The results of the tests are shown in Table 1 below.

TABLE 1

| Catalyst | Ethylene oxide conversion (% w/w) | Selectivity to Glycol Ethers (% w/w) | | By-Products (% w/w) |
| --- | --- | --- | --- | --- |
| | | BMGE | Other Ethers | |
| a. | 45 | 94 | 6 | 0.2 |
| b. | 48 | 95 | 5 | 0.2 |
| c. | 80 | 95 | 5 | 0.3 |
| d. | 29 | 100 | 0 | 0.1 |
| e. | 46 | 100 | 0 | 0.1 |
| f. | 46 | 100 | 0 | 0.1 |

The above results show that the present process achieves a very good conversion and selectivity to the mono-glycol ethers. Moreover, whilst the catalysts with a dichromate phase perform exceedingly well, the selectivity improves to 100% in the case of catalysts which have a polyoxometallate phase of the vanadate or molybdate type.

h. Preparation of decavanadate pillared Mg-Al LDH 20 g of calcined hydrotalcite (obtained from the Kyowa Chemical Industry Co. Ltd., KW-2100, MgO/Al$_2$O$_3$=4.33 wt basis) was added with stirring to sodium vanadate (13.9 g) dissolved in 1 litre of distilled water. The initial pH of 9.25 was adjusted by the addition of 2 M hydrochloric acid to pH 4.5 over a period of 3 hours. After filtration the bright yellow solid was washed with approximately 1 litre of distilled water before being dried at 80° C. for 16 hours.

i. Preparation of divanadate pillared Mg-Al LDH

Kyowa KW-2100 LDH was calcined at 450° C. for 18 hours under nitrogen atmosphere and cooled in a desiccator under dynamic vacuum. 20 g of calcined material was slurried in degassed distilled water (produced by boiling distilled water and cooling under a nitrogen blanket) for 1 hour to ensure maximum dispersion. The mixture was kept under a nitrogen atmosphere to avoid contamination by atmospheric carbon dioxide. A suspension of 30.5 g of sodium vanadate in 1 litre of degassed water (0.25 M) was further degassed with nitrogen at 65° C. for ½ an hour. Then the pH of the solution was increased to 10 by the addition of 2 M NaOH when a clear colourless solution was obtained. This solution was then mixed to the LDH water slurry and the mixture vigorously stirred at 65° C. under a nitrogen atmosphere. After filtration and washing with 2 litres of hot degassed water, the resultant pale yellow product was left to dry in a desiccator under dynamic vacuum. The X-ray powder diffraction pattern of the resulting white powder evidenced a regenerated hydrotalcite-like compound with a δ(003) spacing of 7.8 Å.

j. Preparation of [Mg-Al-Fe(III)(CN)$_6$]-hexacyanoferrate (III) pillared LDH 20 g of calcined Kyowa-2100 LDH was slurried in 1 litre degassed distilled water for 1 hour to ensure maximum dispersion, the mixture being kept under nitrogen to avoid contamination by atmospheric carbon dioxide. A solution of 32.93 g of K$_3$(Fe[CN]$_6$) in 1 litre of degassed distilled water (0.1 M) was further degassed with nitrogen at room temperature for 0.5 hour, and added to the LDH slurry with vigorous stirring. The pale green precipitate was filtered, washed with 2 litres of hot degassed water, and dried in a desiccator.

k. Preparation of re-hydrated calcined Mg-Al-LDH (Comparative Test)

Kyowa-2100 calcined LDH was further calcined at 450° C. under a nitrogen flow for 14 hours. 41.9 g of this material was added to 500 ml of distilled water which had been degassed by purging with a stream of nitrogen. The resulting slurry was heated to 80° C., and stirred under a nitrogen atmosphere for 48 hours. Removal of the water on a rotary evaporator at 80° C. followed by drying at 80° C. gave the final product. The X-ray powder diffraction pattern showed a highly crystalline material with a δ(003) spacing of 7.7 Å.

l. Production of Glycol Ethers using catalysts h–k above

Catalyst (8 g) (meshed in each case to <150 μm) was added to n-butanol (978.6 g) in a stirred 2 litre batch autoclave. After purging with nitrogen, approximately 116 g of ethylene oxide (butanol/ethylene oxide=5.0 on a molar basis) was then added, and the sealed autoclave raised to 120° C. The pressure was then increased to 3000 KPa (30 barg) by applying a nitrogen top pressure, and reaction conditions maintained until the ethylene oxide was consumed. Liquid products were analysed by gas chromatography and the results of the analysis are shown in Table 2 below.

TABLE 2

| Catalyst | Selectivity to Glycol Ethers (% w/w) | | By-products (% w/w) |
| --- | --- | --- | --- |
| | BMGE | Other Ethers | |
| h | 91.6 | 7.8 | 0.6 |
| h (a) | 91.7 | 7.8 | 0.5 |
| i | 83.6 | 15.6 | 0.6 |
| j | 88.4 | 11.6 | 0 |
| k (b) | 80.4 | 19.3 | 0.3 |
| m (b) | 76.1 | 23.8 | 0.1 |

(a) 7.1 g of catalyst recovered from the run above was recycled.
(b) Comparative Test (not according to the invention) using 0.11 g potassium acetate.

Examples (h) to (j) illustrate that higher BMGE selectivities can be obtained with the pillared LDH clay catalysts than with a commercial potassium acetate catalyst (example m). Comparative example (k), using a non-pillared Mg-Al LDH clay shows that BMGE selectivity is reduced if the pillar is omitted. The non-pillared catalyst also lost physical integrity and crystallinity (by X-ray diffraction) under reaction conditions. With the pillared materials the catalyst was easily recovered post reaction, and could be re-cycled with no loss in MBGE selectivity (example h(a)).

What is claimed is:

1. A process for making glycol ethers said process comprised reacting at least one olefin oxide with an alcohol over a catalyst comprising an LDH clay with its layered structure intact and having interlamellar anions comprised substantially of metal anions or (poly)oxometallate anions.

2. A process according to claim 1 wherein the olefin oxide used as reactant is selected from the group consisting of ethylene, propylene, butylene oxide or mixtures thereof.

3. A process according to claim 1 wherein the alcohol used for the reaction is an aliphatic, cycloaliphatic or an aromatic alcohol which may be a mono- di- or poly-hydric alcohol.

4. A process according to claim 3 wherein the alcohol is a monohydric C1–C6 alcohol.

5. A process according to claim 3 wherein the alcohol is selected from the group consisting of methanol, ethanol, the isomeric propanols and the isomeric butanols.

6. A process according to claim 1 wherein the alcohol is used in a molar excess to obtain a monoglycol ether.

7. A process according to claim 6 wherein the molar ratio of alcohol to the olefin oxide is at least 2:1.

8. A process according to claim 1 wherein in the LDH clays, the interlamellar anions present are inorganic metal anions, oxometallate or polyoxometallate anions and include inter alia one or more of the following anions: chromium, vanadium, molybdenum and phosphorus, and (poly)oxoanions thereof.

9. A process according to claim 8 wherein the (poly)oxoanions and (poly)oxometallate anions include both oxoanions and oxometallate anions and the polyoxo derivatives thereof.

10. A process according to claim 9 wherein the catalyst comprises a copper-chromium hydrotalcite anionic clay exchanged with (poly)oxometallate anions.

11. A process according to claim 9 wherein the catalyst comprises a magnesium-aluminium hydrotalcite anionic clay exchanged with (poly)oxometallate anions.

12. A process according to claim 1 wherein the reaction of the olefin with the alcohol in the presence of an LDH clay catalyst is carried out in the liquid phase.

13. A process according to claim 1 wherein the reaction of the olefin with the alcohol in the presence of an LDH clay is carried out at a temperature in the range from ambient to about 250° C.

14. A process according to claim 1 wherein the reaction of the olefin with the alcohol is carried out at a pressure in the range from atmospheric to about 50 bar (5000 KPa).

15. A process according to claim 1 for the reaction of butan-1-ol with one or more units of ethylene oxide to make one or more of butyl-monoglycol ether (BMGE), di-glycol ether (BDGE), tri-glycol ether.

16. The process according to claim 1, wherein said catalyst is employed in an uncalcined form.

* * * * *